(12) United States Patent
Zeltman

(10) Patent No.: US 8,940,326 B2
(45) Date of Patent: Jan. 27, 2015

(54) TRANSDERMAL PATCH AND METHOD FOR DELIVERY OF VITAMIN $B_{12}$

(75) Inventor: Jon D. Zeltman, Kidron, OH (US)

(73) Assignee: Vita Sciences LLC, Airmont, NY (US)

( * ) Notice: Subject to any disclaimer, the term of this patent is extended or adjusted under 35 U.S.C. 154(b) by 1419 days.

(21) Appl. No.: 12/051,370

(22) Filed: Mar. 19, 2008

(65) Prior Publication Data

US 2008/0233180 A1   Sep. 25, 2008

Related U.S. Application Data

(60) Provisional application No. 60/895,571, filed on Mar. 19, 2007.

(51) Int. Cl.

| | |
|---|---|
| *A61F 13/02* | (2006.01) |
| *A61K 31/714* | (2006.01) |
| *A61K 9/70* | (2006.01) |
| *A61K 47/02* | (2006.01) |

(52) U.S. Cl.
CPC ............. *A61K 9/7061* (2013.01); *A61K 31/714* (2013.01); *A61K 47/02* (2013.01)
USPC ............................................ 424/449; 514/52

(58) Field of Classification Search
USPC ......................................................... 424/449
See application file for complete search history.

(56) References Cited

U.S. PATENT DOCUMENTS

| 4,873,266 | A  | * | 10/1989 | Leonard et al. ............... 514/653 |
|---|---|---|---|---|
| 5,300,291 | A  | * | 4/1994 | Sablotsky et al. .......... 424/78.18 |
| 5,362,497 | A  | * | 11/1994 | Yamada et al. ................ 424/449 |
| 2005/0266096 | A1 | * | 12/2005 | Shrivastava et al. .......... 424/638 |
| 2006/0039939 | A1 | * | 2/2006 | Lai et al. ....................... 424/401 |

OTHER PUBLICATIONS

WO 97/36598. Lippman et al.*

* cited by examiner

*Primary Examiner* — Johann R Richter
*Assistant Examiner* — Audrea Buckley
(74) *Attorney, Agent, or Firm* — Quarles & Brady LLP

(57) ABSTRACT

The present invention is directed to compositions and devices for transdermally administering vitamin $B_{12}$ to a subject. In one aspect, a vitamin $B_{12}$ containing composition suitable for transdermal administration is provided in the form of a shelf stable transdermal delivery patch. Such patches contain vitamin $B_{12}$ combined with selected penetration enhancers and vitamin $B_{12}$ stabilizers.

4 Claims, 1 Drawing Sheet

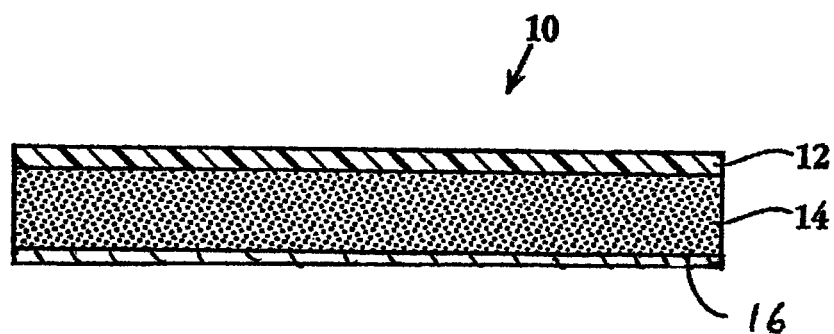

TRANSDERMAL PATCH AND METHOD FOR DELIVERY OF VITAMIN $B_{12}$

CROSS-REFERENCE TO RELATED APPLICATIONS

This application claims priority to U.S. Provisional Application No. 60/895,571, filed Mar. 19, 2007, the entirety of which is hereby incorporated by reference herein.

STATEMENT REGARDING FEDERALLY-SPONSORED RESEARCH OR DEVELOPMENT

Not applicable.

FIELD OF THE INVENTION

This invention relates generally to compositions, devices and methods for administering vitamin $B_{12}$ to human and non-human subjects. More particularly, the invention is directed to shelf-stable vitamin $B_{12}$-containing transdermal delivery patches and methods of their preparation and use.

BACKGROUND OF THE INVENTION

Transdermal patches have been described extensively in the art to deliver drugs and agents other than vitamin $B_{12}$ through intact skin. For example, such devices include, but are not limited to, those described in U.S. Pat. Nos. 3,170,795; 3,598,122, 3,598,123; 3,731,683; 3,742,951; 3,814,097; 3,921,636; 3,972,995; 3,993,072; 3,993,073; 3,996,934; 4,031,894; 4,060,084; 4,069,307; 4,077,407; 4,201,211; 4,230,105; 4,286,592; 4,292,299; 4,292,303; 4,314,557; 4,379,454; and 4,568,343, each of which is hereby incorporated by reference in its entirety.

Transdermal delivery offers several advantages as compared to oral delivery and injection, including, but not limited to: 1) avoidance of hepatic first pass metabolism; 2) discontinuing administration easily accomplished by patch removal; 3) improved patient compliance; and 4) maintenance of constant active agent level in blood for longer periods of time. As specifically compared to oral delivery, transdermal delivery decreases the necessary dose to be administered.

The major obstacle to transdermal delivery is the excellent barrier characteristics exhibited by skin. Several routes through the skin have been identified. The transappendageal route transports substances through sweat glands and hair follicles with their sebaceous glands. This route is considered of minor importance due to the very limited area (less than 0.1% of total skin surface). However, large compounds can theoretically be delivered by this route. The transepidermal route consists of transport via diffusion through the cellular layer that includes the stratum corneum (consisting of lipids), viable epidermis (90% water held together by tonofibrils), and dermis (loose connective tissue composed of fibrous protein embedded in an amorphous ground substance).

Increased penetration of the skin barrier is achieved by use of physical methods, biological methods, and chemical penetration enhancers. Physical methods include iontophoresis, sonophoresis, thermal energy, and stripping of the stratum corneum. The biological approach utilizes a therapeutically inactive prodrug that is transported through the skin barrier by physiological mechanisms with the prodrug then being metabolized to produce the therapeutically active drug. Chemical penetration enhancers reversibly decrease the barrier allowing drug permeation.

Ideal enhancers are generally non-toxic, pharmacologically inert, nonallergenic, predictable with immediate effect, amendable to full barrier recovery after removal, compatible with a drug and adjuvants, and cosmetically acceptable. Penetration enhancers can be classified broadly as fatty acids, fatty alcohols, terpenes, sulfoxides, anionic surfactants, cationic surfactants, nonionic surfactants, zwitterionic surfactants, polyols, amides, ureas, lactam, and sugars. The actual mechanism of action by a penetration enhancer may be one or more of the following: 1) disruption of the ordered structure of stratum corneum lipids; 2) interaction with intracellular protein; or 3) improved partitioning of the drug, co-enhancer or solvent into the stratum corneum. It has been found that enhancer mixtures can be more efficient by acting together on one or more of these mechanisms to facilitate permeation.

Dimethyl sulfoxide (DMSO) was recognized over 40 years ago for its ability to open the skin. Hundreds of formulations have since been investigated as potential penetration enhancers. Unfortunately, no reliable means for predicting permeability efficacy yet exist although simple guidelines have been proposed.

It has been demonstrated that macromolecules (1-10 kDa) are able to pass through the skin when mixtures of penetration enhancers are applied. In particular, a mixture of sodium dodecyl sulfate and phenyl piperazine increased skin permeability up to 100-fold for macromolecular drugs including heparin, leutinizing hormone releasing hormone and oligonucleotides.

Unfortunately, vitamin $B_{12}$ administration by the transdermal route was previously believed to be problematic due to the large size of the vitamin $B_{12}$ molecule. Cyanocobalamin has a standard molecular weight of 1355. This is considered a large molecule that the skin barrier normally blocks. It is generally understood that molecules of molecular weights of 350 or lower are free to penetrate the dermis. Accordingly, the large molecular size was commonly believed to result in low skin permeation rates and, consequently, sub-optimal vitamin $B_{12}$ dosages imparting no or negligible health benefits to a subject. In addition, cyanocobalamin is sensitive to ultraviolet radiation due to its inherent organometallic character, so it requires stabilization in order to provide a product with practical shelf-life. To be particularly useful as an over the counter product, any transdermal device for vitamin $B_{12}$ delivery would therefore need to overcome issues related to at least skin permeation efficiency and shelf life stability.

SUMMARY OF THE INVENTION

The present invention is directed to transdermal delivery patches for administering vitamin $B_{12}$ and related methods of use and manufacture that overcome the technical drawbacks mentioned above. In particular, the present invention provides shelf stable transdermal delivery patches for administering vitamin $B_{12}$ which impart the respective molecule in an amount sufficient for release at a skin permeation rate sufficient to achieve a health benefit in a subject.

In a first aspect, the present invention provides a shelf stable transdermal delivery patch for administering vitamin $B_{12}$ to a subject. Such a delivery patch includes: (a) a backing layer; (b) a skin contact adhesive layer adjacent to the backing layer, the skin contact adhesive layer including: (i) a polymeric adhesive; (ii) vitamin $B_{12}$; (iii) a penetration enhancer effective to enhance transdermal uptake of vitamin $B_{12}$ by the subject; and (iv) a vitamin $B_{12}$ stabilizer to stabilize the vitamin $B_{12}$ contained within the adhesive layer; and (c) a removable impermeable layer overlaying the skin contact adhesive layer, the removable impermeable layer preventing vitamin $B_{12}$ release from the skin contact adhesive layer prior to use.

Polymeric adhesives useful in the adhesive layer of transdermal patches of the invention include, but are not limited to, polyacrylate polymers, rubber-based adhesives, and polysiloxanes adhesives. Acrylic co-polymer is a preferred polymeric adhesive, particularly when provided in the adhesive layer at about 40 wt % to about 95 wt %, most preferably at about 82 wt %.

The transdermal delivery patch of the invention contains vitamin $B_{12}$, preferably at about 0.1 wt % to about 25 wt % of the skin contact adhesive layer's dry weight, most preferably at 4.0 wt %. Transdermal deliver patches further contain penetration enhancers, most preferably as a combination of: (a) menthone at about 1.3 wt % to about 12.0 wt %; and (b) propylene glycol at about 0.8 wt % to about 12 wt %, based on the skin contact adhesive layer's dry weight. Other alternative penetration enhancers include, but are not limited to, nicotinates, fatty acids, fatty alcohols, terpenes, polyols and combinations thereof.

Delivery patches according to the invention have an adhesive layer that, in addition, includes a vitamin $B_{12}$ stabilizer such as, e.g., ascorbic acid, phosphoric acid, panthenoic acid, butylated hydroxytoluene, edetic acid, nicotinic acid, sodium selenite, and combinations thereof. Sodium selenite is a preferred stabilizer, most preferably when provided at about 0.01 wt % to about 1.2 wt % of the adhesive layer's dry weight. In general, such stabilizers function as anti-oxidants which prevent oxidative degradation of the vitamin $B_{12}$.

A most preferred composition for use in transdermal delivery contains acrylic copolymer at about 82 wt %, vitamin $B_{12}$ at about 4.0 wt %, menthone at about 5.0 wt %, propylene glycol at about 3.5 wt %, and sodium selenite at about 0.2 wt %.

In a second aspect, the present invention encompasses a method of transdermally administering vitamin $B_{12}$ to a subject. Such a method includes steps of contacting a subject's skin with a composition including: (a) a polymeric adhesive; (b) vitamin $B_{12}$; (c) a penetration enhancer effective to enhance transdermal uptake of the vitamin $B_{12}$ by the subject; and (d) a vitamin $B_{12}$ stabilizer to stabilize the vitamin $B_{12}$ contained within the composition.

The composition is preferably provided in the form of a shelf stable transdermal delivery patch as described and claimed herein. A subject may be any animal, most preferably, a human.

In yet another aspect, the invention is directed to a shelf stable composition useful for the transdermal delivery of vitamin $B_{12}$ to a subject. Such a composition is useful in the preparation of transdermal delivery patches according to the invention. Although transdermal patches may be manufactured by various methods, a preferred method is a roller-coating process. Such a process includes steps of roller-coating a composition comprising: (i) vitamin $B_{12}$ at about 0.1 wt % to about 15 wt %; (ii) sodium selenite at about 0.01 wt % to about 1.0 wt %; (iii) menthone at about 0.8 wt % to 12 wt %; (iv) propylene glycol at about 0.5 wt % to about 12 wt %; (v) nonionic surfactant at about 0.1% to about 1.0 wt %; (vi) polyurethane polymer associative thickener at about 0.6 wt % to about 6 wt %; (vii) added water at about 0.3 wt % to about 50 wt %; and (viii) acrylic co-polymer at about 40.0 wt % to about 97.6 wt %; onto an impermeable release layer to form a skin contact adhesive layer adjacent to the release layer. Water is then evaporated from the composition by heating the composition itself to a temperature no greater than about 215 degrees F., preferably no more than 200 degrees F. A backing layer is then laminated to the skin contact adhesive layer and the resulting multilayered product is cut into a pre-selected shape and size thereby providing a shelf stable transdermal delivery patch.

Other objects, features and advantages of the present invention will become apparent after review of the specification, claims and drawings.

BRIEF DESCRIPTION OF THE DRAWING

FIG. 1 shows a transdermal patch having an impermeable backing layer 12, skin contact adhesive layer 14 containing vitamin $B_{12}$, and a removable impermeable layer 16.

DETAILED DESCRIPTION OF THE INVENTION

Before the present compositions, devices and methods for achieving specified vitamin $B_{12}$ transdermal delivery are disclosed and described, it is to be understood that this invention is not limited to the particular process steps and materials disclosed herein, but is extended to equivalents thereof as would be recognized by those ordinarily skilled in the relevant arts. It should also be understood that terminology employed herein is used for the purpose of describing particular embodiments only and is not intended to be limiting.

A. Definitions

In describing and claiming the present invention, the following terminology will be used. The singular forms "a" "an," and, "the" include plural referents unless the context clearly dictates otherwise. Thus, for example, reference to "a vitamin $B_{12}$ molecule" includes reference to one or more of such molecules, and reference to "a fatty acid" includes reference to a mixture of two or more of such fatty acids.

As used herein, the term "vitamin $B_{12}$" refers to the water soluble vitamin cyanocobalamin which is an organometallic compound with a trivalent cobalt ion bound inside a corrin ring. Vitamin $B_{12}$ is important in animals for, generally, maintaining healthy metabolism regulation, red blood cell production, and healthy central nervous system maintenance. Vitamin $B_{12}$ useful in the present invention may be found in or derived from any synthetic or natural source, and the term "vitamin $B_{12}$" shall refer to the analogues, derivatives, salts, and prodrugs, of vitamin $B_{12}$, as well as mixtures thereof. Further, vitamin $B_{12}$ analogues, derivatives, salts, and prodrugs may be obtained by synthesis, extraction as a natural product from one or more bacteria, animal or plant species, or by partial extraction and further synthesis. Methylcobalamin and 5-deoxyadenosyl cobalamin are the forms of vitamin $B_{12}$ used in the human body. The form of cobalamin used in most supplements, cyanocobalamin, is readily converted by the body to 5-deoxyadenosyl and methylcobalamin.

As used herein, "vitamin $B_{12}$ delivery composition," "vitamin $B_{12}$ transdermal delivery patch," "transdermal delivery composition," "transdermal delivery formulation," or "transdermal formulation" refer to any vitamin $B_{12}$ containing device, system, product, chemical combination, or mechanism capable of being applied to, or against the skin, to effect transdermal delivery, of vitamin $B_{12}$.

The term "subject" refers to an animal, most preferably a human, that derives a health benefit from the administration of vitamin $B_{12}$.

As used herein, the term "skin" refers to any membrane of the animal body, preferably human body, to which a chemical formulation or composition may be applied including the external skin of the body, the mucosa membranes of the nasal, oral, vaginal, and rectal cavities.

As used herein, the term "transdermal" or "percutaneous" delivery means delivery of a substance or agent, by passage into and through the skin. Hence the terms "transdermal" and "transmucosal" are used interchangeably unless specifically stated otherwise. Likewise, the terms "skin", "derma", "epidermis", "mucosa", and the like shall also be used interchangeably unless specifically stated otherwise.

As used herein, the terms "enhancement", "penetration enhancement", or "permeation enhancement" refer to an increase in the permeability of the skin, to a delivery substance or agent, so as to increase the rate at which the delivery substance permeates through the skin. "Permeation enhancer", "enhancer", "penetration enhancer", or similar terms refer to a material, or materials that achieve or facilitate such permeation enhancement, and an "effective amount" of an enhancer means an amount effective to enhance penetration through the skin, of vitamin $B_{12}$, to a selected degree. Accordingly, the terms "skin permeation rate" and "transdermal permeation rate" refer to the rate at which the delivery substance, in this case vitamin $B_{12}$, permeates through the skin. An in-depth overview of penetration enhancers is presented by Kanikkannan et al., (*Current Medicinal Chemistry*, 1999 Volume 6, No. 7). An index of permeation enhancers is also disclosed by Osborne et al., (*Pharmaceutical Technology*, June 1998), both of which are incorporated by reference herein. Enhanced permeation as affected through the use of such enhancers can be observed, for example, by measuring the rate of diffusion of the delivery substance through animal or human skin using a diffusion cell apparatus. Such a diffusion cell is described by Merritt et al., (*J. Controlled Released*, 61 1984), incorporated herein by reference.

By the term "skin contact adhesive layer" is meant a predetermined amount of vitamin $B_{12}$ dissolved or suspended in a polymeric carrier or phase, in one aspect a pressure-sensitive adhesive, that can also contain other ingredients, and in which a permeation enhancer, stabilizer and other positive health benefit promoting substances are also dissolved or suspended. This definition is meant to include embodiments wherein such polymeric phase is used within an overlay adhesive to form an adhesive patch with a reservoir. The transdermal patches described and claimed herein are passive diffusion patches. A "passive diffusion patch" as used herein is a transdermal patch which is arranged to deliver the vitamin $B_{12}$ across the skin by passive diffusion rather than utilizing an electric field.

A patch system according to the invention comprises an adhesive layer having a film backing laminated onto the distal surface thereof and, before transdermal application, an impermeable release liner on the proximal surface of the adhesive. The film backing protects the polymeric phase of the patch and, in certain embodiments, totally prevents release of the delivery substance and/or enhancer to the environment. While an impermeable (i.e., occlusive) backing is preferred, a non-occlusive backing layer may be utilized so long as packaging of the patch is fully occlusive to prevent loss of adhesive layer components to the environment. The release liner functions similarly to the impermeable backing, but is removed from the patch prior to application of the patch to the skin as defined above. Patches are known in the art of transdermal delivery to routinely contain such backing and release liner components, and patches according to the present invention should be considered to comprise such backing and release liner or their functional equivalents. An adhesive layer therefore includes a unit dosage form, or type of formulation, which includes a predetermined amount of vitamin $B_{12}$, permeation enhancer, stabilizer, as well as other optional ingredients, such as good health-imparting ingredients, in a polymeric carrier.

The term "shelf stable", when used in the context of transdermal devices and compositions described and claimed herein, refers to the ability of those materials to withstand long term storage and, upon use, deliver an amount of vitamin $B_{12}$ sufficient for release at a skin permeation rate sufficient to achieve a health benefit in a subject. Devices and compositions according to the invention shall preferably have a shelf life of at least 24 months under transport and storage conditions regularly imposed on vitamin supplements by manufacturers, carriers, retailers, and providers of such products.

As used herein, "inert carrier" refers to a polymeric carrier, or other carrier vehicle into which vitamin $B_{12}$ may be admixed in order to form a transdermal delivery formulation. Inert carriers must generally be pharmaceutically acceptable, in that they are suitable for administration to the skin without causing significant instances of adverse results. Further, inert carriers must not react with the active substance to substantially degrade it, or otherwise form impurities, which may be delivered to the skin.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a concentration range of 0.5 to 400 ng/ml should be interpreted to include not only the explicitly recited concentration limits, but also to include individual concentrations within that range, as well as sub-ranges. This interpretation should apply regardless of the breadth of the range or the characteristic being described. All weight percentages (wt % s) are based on a dry weight of the described composition, unless explicitly noted otherwise.

B. The Invention

A transdermal delivery device, also referred to herein as a transdermal patch, suitable for use for delivery of vitamin $B_{12}$ is now described. FIG. 1 illustrates transdermal patch 10, and a basic embodiment of the present invention. Patch 10 includes an impermeable backing layer 12 and a skin contact adhesive layer 14 which serves both as a reservoir for vitamin $B_{12}$ and as a means of attaching the device to the skin of a subject. Adhesive layer 14 includes, in addition to vitamin $B_{12}$, a permeation enhancer, and a vitamin $B_{12}$ stabilizer. The adhesive layer's surface is a vitamin $B_{12}$ permeable contact surface and is adapted to be placed against the patient's skin. Patch 10 further includes a removable impermeable layer 16, also referred to in the art as a release liner or removable peel strip, covering the adhesive layer's surface during storage and prior to use to prevent vitamin $B_{12}$ release from adhesive layer 14.

In a preferred embodiment, backing layer 12 functions as an occlusive layer that prevents loss of vitamin $B_{12}$, enhancers and stabilizers present in the adhesive layer to the environment. Materials suitable for use as the backing layer are known to those of skill in the art. The backing layer is preferably opaque to protect components of the matrix patch from degradation caused by exposure to ultraviolet light, particularly the organometallic vitamin $B_{12}$ molecule. Further, the backing should be capable of binding to and supporting the adhesive layer, yet should be pliable to accommodate the movements of a person using the patch. It is also preferable for manufacturing purposes that the backing layer be mechanically strong enough to form a support onto which the vitamin $B_{12}$-enhancer-stabilizer loaded adhesive can be brought into contact with the subject's skin.

Many polymers are useful for making backing layers, such as polyvinylchloride, polyvinylidene chloride, polyolefins, polyethylene, polypropylene, polyurethane, and polyesters. Exemplary backing material are polyester or aluminized polyester, such as the Scotchpak (registered trademark) medical films available from 3M Corporation (St. Paul, Minn.). In addition to these materials, polyamides, metal vapor deposited films or sheets thereof, rubber sheets, films, expanded synthetic resin sheets, unwoven fabrics, fabrics, knitted fabrics, papers, and foils may also be used. The materials may be laminated, pigmented or metalized. The preferred backing material is VOLARA (registered trademark) closed-cell polyethylene EVA copolymer ⅟₃₂" thick foam manufactured by Sekisui Voltek (Lawrence, Mass.). This material is available in a range of standard colors as well as custom matched colors. Thickness is a desirable feature of the patch making it easier to manipulate by subjects with arthritic fingers.

Although backing layers may be prepared directly from raw materials, they may also be obtained as films from commercial sources. For instances, 3M Corporation, St. Paul Minn.; Dow Chemicals, Midland, Mich.; Avery Specialty Tape Division, Painsville, Ohio; and A.F. Packaging, Winston-Salem, N.C., all supply commercially available films which can be used for backing layers. One type of backing layer which is commercially available from 3M Corporation is the Scotch Pak 1000 (registered trademark). The backing layer may be made from Scotch Pak 1006 or 1009 (registered trademarks), which are skin colored aluminized polyester films of 50 microns in thickness. Another type of backing layer is 3M-1012 which is a transparent polyester film laminate. Each of these commercially available backing layers is sold by 3M Corporation.

Adhesive layer 14 in this embodiment serves both as a reservoir for vitamin $B_{12}$ and as contact surface for placement against a subject's skin. The vitamin $B_{12}$ is dispersed in the adhesive layer. As used herein, the term "dispersed" refers to the distribution of vitamin $B_{12}$ throughout the adhesive layer.

Adhesive layer 14 shown in FIG. 1 may be prepared by mixing together a solution of the polymeric adhesive (or, equivalently, adhesive polymer), which can be purchased commercially or prepared by dissolving the adhesive solid in a suitable solvent, with a solution of vitamin $B_{12}$ dissolved or evenly dispersed in selected enhancers and stabilizers. The mixture may be poured into a mold or cast alone or on the desired backing material. The casting is then left for the solvent to evaporate at room temperature or in an oven at a slightly elevated temperature. After solvent evaporation, the adhesive matrix takes the form of an adhesive polymer film typically having a thickness in the range of about 6 to 100 microns. Alternatively, a $B_{12}$ solution can be incubated with a precast adhesive laminate to allow the vitamin $B_{12}$ to diffuse into the adhesive layer.

The amount of vitamin $B_{12}$ loaded into the adhesive layer can be varied by varying the concentration of vitamin $B_{12}$ in the casting mixture and the thickness of the adhesive layer. The amount of vitamin $B_{12}$ in the adhesive layer of a given patch area should be sufficient to provide for at least 8 hours of treatment, more preferably 24 hours of treatment and most preferably for 48 hours of treatment. However, longer treatment times may certainly be utilized to optimize efficiency of vitamin delivery. In certain embodiments, the adhesive layer is formulated to allow the patch to detach from the subject in a predetermined amount of time, such as two days from application to detachment. This prompts the user to apply a new patch and also encourages the user to rotate the skin area directly within patch contact. As can be appreciated, the amount of vitamin $B_{12}$ present in the patch depends on several factors, such as the desired time frame for release of the vitamin, the particular components provided with the vitamin $B_{12}$, and the permeability of the adhesive layer. In a preferred embodiment, the vitamin $B_{12}$ is present in the adhesive layer at about 0.1 wt percent to about 25 wt percent, more preferably at about 1 wt percent to about 8 wt percent, and most preferably at about 4 wt percent. Vitamin $B_{12}$ suitable for use in the present invention is available from Charles Bowman & Co (Holland, Mich.).

The transdermal device includes an enhancer effective to increase the skin permeation rate of vitamin $B_{12}$ to the skin. Such enhancers are necessary to overcome the low skin permeation rate of vitamin $B_{12}$, when administered alone. Enhancers useful in the present invention include nicotinates, fatty acids, fatty alcohols, terpenes, polyols and combinations thereof, with a combination of menthone and propylene glycol being most preferred.

Various stabilizers, alternatively referred to as preservatives, are used to stabilize the vitamin $B_{12}$ contained within the transdermal patch. The type of stabilizer selected will depend on the type of components used within the vitamin $B_{12}$ composition as well as the other materials of the patch. Suitable stabilizers include, ascorbic acid, phosphoric acid, panthenoic acid, butylated hydroxytoluene, edetic acid, nicotinic acid, sodium selenite, and combinations thereof. Sodium selenite is the preferred vitamin $B_{12}$ stabilizer in formulations according to the invention. Stabilizers may further include, but are not limited to, alcohols, e.g., ethanol or isopropanol; quaternary ammonium surfactants, as well as many other preservative compounds known in the art. The United States Pharmacopeia XXI 1985 includes a section which describes parameters for selecting compounds useful in enhancing the stability of various drugs (pp. 1345-1347). Other factors, such as pH and ionic strength of the solution, also influence the stability of the compounds within the adhesive layer.

The adhesive used in an adhesive type patch can be selected from a variety of adhesives available commercially and known to those in the art. For example, common adhesives are those based on poly isobutylene, acrylic, and silicone. The adhesive selected will depend in part on the enhancer or enhancers chosen and the amount of vitamin, enhancer and stabilizer loaded into the adhesive layer. The adhesive must retain its adhesive properties in the presence of these additives, and provide anchorage to the backing film, tack for good instantaneous adhesion to the skin, good adhesion throughout the treatment period and clean removal from the skin after treatment. Some preferred adhesives include those available from Dow Corning Corporation, Air Products Corporation, Cytek Surface Specialties and from National Starch and Chemical Company.

A wide range of adhesives useful in connection with transdermal patches will be known to those skilled in the art of transdermal drug delivery. In one aspect of the invention, acceptable adhesives may include polyacrylate polymers, rubber-based adhesives, and polysiloxanes adhesives. These types of materials, as well as others, are described by Van Norstrand (*The Handbook of Pressure Sensitive Adhesive Technology* Second Edition 1989), which is hereby incorporated by reference.

In one aspect, polyacrylate polymers can be any of the homopolymers, copolymers, terpolymers, and the like of various acrylic acids. In another aspect of the invention, the acrylate polymers may be a combination of one or more monomers of acrylic acids and other copolymerizable monomers.

Acrylate polymers may also include copolymers of alkyl acrylates and/or methacrylates, and/or copolymerizable secondary monomers or monomers with functional groups. The adhesive material may be an acrylic adhesive including at least one polymer selected from homopolymers of acrylic esters, copolymers of two or more types of acrylic ester units and copolymers of acrylic esters and other functional monomers. Acrylic esters include, but are not limited to, butyl (meth)acrylate, pentyl (meth)acrylate, hexyl (meth)acrylate, heptyl (meth)acrylate, octy (meth)acrylate, nonyl (meth)acrylate, decyl (meth)acrylate, etc. Functional monomers include, but are not limited to, monomers containing a hydroxyl group, such as hydroxyethyl (meth)acrylate, hydroxypropyl (meth)acrylate, etc., monomers containing a carboxyl group, such as carboxyl methacrylate, etc. and monomers containing an amide group such as methacrylamide, dimetheylmethacrylamide, etc.

Specific examples of acrylate monomers, which are suitable for use with the present invention include, but are not limited to methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecylmethacrylate, tridecyl acrylate, tridecyl methacrylate, and mixtures thereof.

Specific examples of functional monomers which are copolymerizable with the above-recited alkyl acrylates or methacrylates, which can also be used include, but are not limited to acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxethyl acrylate, methoxyethyl methacrylate, and mixtures thereof.

Further details and examples of acrylic adhesives which are suitable for use in the present invention are set forth in Satas (*The Handbook of Pressure-sensitive Adhesive Technology* 2nd Ed. Pp. 396-456 1989), which is incorporated herein by reference in its entirety.

Examples of suitable acrylic adhesives which are commercially available include polyacrylate adhesives sold under the trademarks DUROTAK (registered trademark) by National Starch and Chemical Corporation, Bridgewater, N.J., as well as GELVA-MULTIPOLYMER SOLUTION (registered trademark) by Cytek Surface Specialties, Smyrna, Ga. Other examples of adhesives, and adhesive formulations, which can be used in connection with the present invention are disclosed in U.S. Pat. No. 5,656,286, which is incorporated herein by reference in its entirety.

In one aspect, utilizing a mixture of two or more acrylic polymers may facilitate sustained release of vitamin $B_{12}$. Many variations and combinations of acrylics may be employed to achieve the desired increase in release duration. Examples of such combinations may be found in U.S. Pat. No. 6,024,976, which is incorporated herein by reference in its entirety. Other examples of such acrylic combinations will be readily recognized by those skilled in the art.

Specific examples of suitable rubber-based pressure sensitive adhesives include, but are not limited to hydrocarbon polymers, such as natural and synthetic polyisoprenes, polybutylenes and polyisobutylene (PIB), styrene/butadiene polymers, styrene-isoprene-styrene block copolymers, hydrocarbon polymers such as butyl rubber, halogen-containing polymers such as polyacrylic nitrile, polytetrafluoroethylene, polyvinyl chloride, polyvinylidene chloride, and polychlorodiene, and polysiloxanes, and other copolymers thereof.

Specific examples of suitable polysiloxanes include but are not limited to silicone pressure sensitive adhesives, which are a based on two major components: a polymer, or gum, and a tackifying resin. The polysiloxane adhesive may be prepared by cross-linking the gum, typically a high molecular weight polydiorganosiloxane with the resin to produce a three-dimensional silicate structure via a condensation reaction in an appropriate organic solvent. Various aspects of formulating polysiloxane adhesives are known in the art. Suitable silicone pressure-sensitive adhesives are commercially available and include the silicone adhesives sold under the trademark BIO-PSA (registered trademark) Dow Corning Corporation, Medical Products, Midland, Mich.

The adhesive layer can further comprise various additives in addition to the vitamin, permeation enhancer and stabilizer that are the fundamental components of the adhesive patch formulation. These additives are generally those pharmaceutically acceptable ingredients that are known in the art of transdermal substance delivery and, more particularly, in the art of transdermal substance delivery. However, such additive ingredients must not materially alter the basic and novel characteristics of the patch. For example, suitable diluents can include mineral oil, low molecular weight polymers, plasticizers, and the like. Many transdermal delivery substance formulations have a tendency to irritate the skin after prolonged exposure thereto, thus addition of a skin irritation reducing agent aids may be desirable.

In order to enhance the ability of the adhesive layer to attach to the skin, it may optionally contain a tackifier. Tack can be controlled by combining adhesives of varying hardnesses (glass temperature or $T_g$). Tackifier is a polymer which is insoluble in water and composed of a monomer which contains partly or wholly a (meth)acrylic alkyl ester. Such types of polymers include, but are not limited to, acrylic, N-butyl-methacrylic copolymer (Primal N580NF, sold by Japan Acrylic Chemical Company, Ltd.), acrylic methyl, acrylic 2-ethylhexyl copolymer (Nikasol TS-6520, sold by Nippon Carbide Industries Company, Ltd.), polyacrylic acid (Jurymer AC-10LPH, sold by Nihon Junyaku Company, Ltd.), methacrylic copolymer L (Plastoid L50, sold by Rohm Pharma GmbH), and aminoalkylmethacrylate copolymer E (Plastoid E35L, Plastoid E35M, Plastoid E35H, all sold by Rohm Pharma GmbH).

In a preferred embodiment, the adhesive layer is formed from a shelf stable composition having the following formulation: (a) vitamin $B_{12}$ at about 4 wt %; (b) sodium selenite at about 0.2 wt %; (c) menthone at about 5 wt %; (d) propylene glycol at about 3.5 wt %; (e) nonionic surfactant at about 1 wt % (f) polyurethane polymer associative thickener at about 2 wt %; and (g) acrylic co-polymer at about 82.3 wt %.

Referring again to FIG. 1, transdermal patch 10 includes a release liner 16 which is positioned adjacent to the surface of adhesive layer 14 and which is removed prior to application of the transdermal patch to the skin. Liner 16, which is used to cover the adhesive backing during storage to prevent a evaporative loss of the vitamin composition and shield the same from ultraviolet light damage during storage, may be made from any impermeable film. It may be made from the same impermeable material as the backing layer or it may also be a metal foil, Mylar (registered trademark) polyethylene terephthalate, siliconized polyester, fumed silica in silicone rubber, polytretrafluoroethylene, cellophane, siliconized paper, aluminized paper, polyvinyl chloride film, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene. A thickness of about 0.0005 to about 0.01 inch is preferred. The preferred release liner is about 0.004 inch siliconized opaque polyester.

A preferred method of manufacturing a shelf stable transdermal delivery patch according to the invention is via a roller-coating process. In general, this process includes roller-coating a vitamin $B_{12}$ containing composition onto an impermeable release liner layer to form a skin contact adhesive layer adjacent to the release liner layer. Water contained within the composition is then evaporated by heating the composition to a temperature no greater than about 215 degrees F. for a predetermined amount of time. A backing layer is then laminated to the skin contact adhesive layer, thus transferring the adhesive layer to the backing layer and the resulting multilayered product is cut into a pre-selected shape and size thereby providing a suitable transdermal delivery patch.

U.S. Pat. No. 5,466,465 describes the use of a visible indicator for which changes in color indicate the status of the active agent within the patch. As adapted by routine experimentation for the present use, the indicator may display one color when the patch contains a significant amount of vitamin $B_{12}$, but as the amount is depleted, the color changes to indicate that depletion. The use of the visual indicator can be of help to the subject to determine whether it is necessary to apply an additional patch. The entire contents of U.S. Pat. No. 5,466,465 are incorporated herein by reference.

The transdermal patch may be of any shape, such as oblong, square, round, rectangular, etc. The transdermal patch may also have a variety of sizes. The total surface area in general may range from 1-400 $cm^2$. The actual surface area will depend upon a number of factors, including the amount of vitamin $B_{12}$ to be delivered over a specified period of time, and the presence of permeation enhancers as well as the type of adhesive layer. Preferred patch size is about 2 $cm^2$.

U.S. Pat. No. 5,473,966 describes a method for sizing transdermal patches. The method is useful for reducing the size of the patch, and thus the amount of active ingredient within the patch which will be administered. By routine optimization, the method can be used to customize patches for release profiles of vitamin $B_{12}$ over specific periods of time. For instance, if a subject were using a 50 $cm^2$ patch and desired to use one third less active agent, it would be possible to reduce the patch area to 33 $cm^2$ following such a method, or using any such method known in the art.

The patches are generally stored in pouches which will prevent contamination and prevent damage associated with environmental conditions such as light and dryness. Foil pouches are particularly useful. Many types of storage pouches are commercially available, such as those available from Lithotype Company (San Francisco, Calif.; polyethylene, surlyn), James River Corporation (San Leandro, Calif.; polypropylene metalized film), Ivers-Lee, a division of Becton-Dickinson (West Caldwell, N.J.; 305W, 406), Jefferson Smurfet (Alton, Ill.; acrylonitrile butadiene copolymer film laminate).

The effect of the transdermal patches taught and claimed herein can be assessed using qualitative measures reported by the subject wearing the patch. That is, the patient may decide whether the patch has beneficial effects during wear and for a defined period of time after wearing the patch. These types of qualitative assessment tests have been used successfully to evaluate many types of treatments for chronic illnesses as well as addictions. The simplest form of qualitative analysis involves the use of a vitamin $B_{12}$ patch for some experimental subjects and placebos for others. Each subject determines whether the treatment improved, worsened or made no change in pre-selected health categories.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

C. Examples

Example 1

Transdermal Delivery Patch for Vitamin $B_{12}$

The present example describes the preferred embodiment for the manufacture and formulation of a transdermal patch according to the invention. For aesthetic and consumer ease-of-use, polyethylene foam (1/32" thick) [available under the tradename VOLARA from Voltek] was selected as the fabric-style impermeable backing layer. White silicone-treated-polyester, about 4 mil thick, gives the liner enough stiffness to be easily handled by an arthritic subject.

An emulsion based adhesive was chosen to ease the incorporation of vitamin $B_{12}$ although solvent based adhesives (such as polyisobutylene, polydimethylsiloxane, or acrylate copolymers) could have been chosen. Other key considerations included controlling skin irritation levels of the adhesive including modifiers, proper anchorage of the adhesive to the backing, sufficient skin tackiness to adhere for up to 24 hours yet release without damaging the skin, and wet adhesive characteristics that allow roller coating.

Acrylic co-polymer [Flexbond AV190 adhesive by Air Products] was chosen as a low skin irritation pressure sensitive adhesive (PSA) that bonds better with polyethylene, has a low tendency to re-emulsify by extended contact with skin moisture, and it's capacity for high solids loading. Although the preferred formulation did not include a tackifier, tackiness of the finished adhesive may be controlled by addition of another acrylic copolymer (including those with amino or carboxyl groups) and/or adding tackifers (rosin esters, hydrogenated rosins, dipropylene glycol dibenzoate, and/or mixed hydrocarbons), most preferably the acrylic co-polymer [Flexbond 150 adhesive by Air Products].

Permeation enhancers identified as useful for this product included nicotinates (methyl and benzyl), fatty acids (oleic acid, undecanioic acid, lauric acid), fatty alcohols (octanol and nonanol), terpenes (menthol, limonene, and menthone), and polyols (polyethylene glycol, propylene glycol, and glycerol). In an early trial, a binary enhancer system of methylnicotinate and propylene glycol was used but the inventor observed that the methylnicotinate crystallized after about 3-4 months in the patch. This crystallization resulted in areas of high concentrations of methylnicotinate that could potentially cause severe skin irritation after several hours of wear. Substituting benzylnicotinate resulted in the same severe and unacceptable skin irritation. However, the inventor subsequently found menthone to be an excellent permeation enhancer in conjunction with propylene glycol.

Stabilizers for vitamin $B_{12}$ included ascorbic acid (plus related mineral ascorbates and fatty acid esters), phosphoric acid, panthenoic acid (plus related alcohols and/or salts), butylated hydroxytoluene (BHT), edetic acid (EDTA), nicotinic acid (plus niacinamide), and sodium selenite. Although sodium selenite is used in the existing product, inclusion of a form of nicotinic acid has potential benefits beyond stabilization and may extend the benefits of the overall product; the inclusion of vitamins $B_3$ and $B_6$ are believed to act as antioxidant stabilizers of vitamin $B_{12}$.

To achieve controlled coating thicknesses using a roller-coater method on silicone-treated Mylar, the wet adhesive required thickening using either polyvinyl alcohol, polyethylene oxide polymers, and/or an associative thickener. The polyurethane polymer associative thickener [Rheolate 288 (rheologic additive) by Elementis Specialties] was found to be most effective. Addition of a nonionic surfactant [Surfynol 420, a surfactant by Air Products] provided effective wetting of the Mylar during coating. Table 1 below provides ranges of formulation components (both wet and dry wt % s) for a preferred polymeric adhesive composition according to the invention.

TABLE 1

|  | Minimum | | Maximum | |
| --- | --- | --- | --- | --- |
|  | Wet | Dry | Wet | Dry |
| Cyanocobalamin | 0.1% | 0.1% | 15.0% | 25.0% |
| Sodium Selenite | 0.01% | 0.01% | 1.0% | 1.2% |
| Menthone | 0.8% | 1.3% | 12.0% | 12.0% |
| Propylene glycol | 0.5% | 0.8% | 12.0% | 12.0% |
| Nonionic surfactant | 0.1% | 0.2% | 1.0% | 1.0% |
| Thickener | 0.6% | 1.0% | 6.0% | 8.0% |
| Added Water | 0.3% | 0.0% | 50.0% | 0.0% |
| Acrylic emulsion adhesive | 40.0% | 40.0% | 97.6% | 95.0% |

The formulation for a particularly preferred polymeric adhesive composition is shown below in Table 2:

TABLE 2

|  | Wet Basis | Dry Basis |
| --- | --- | --- |
| Cyanocobalamin | 2.2% | 4.0% |
| Sodium Selenite | 0.1% | 0.2% |
| Menthone | 2.7% | 5.0% |
| Propylene glycol | 1.9% | 3.5% |
| Nonionic surfactant | 0.5% | 1.0% |
| Polyurethane associative thickener | 1.1% | 2.0% |
| Added Water | 10.9% | 0.0% |
| Acrylic copolymer adhesive | 80.5% | 84.3% |

The coating process incorporated rollers to pick up wet adhesive and apply a controlled thickness of 0.002 inches to the silicone-treated side of the Mylar. The wet adhesive on the Mylar was then transported to a forced air oven operating at 300 degrees Fahrenheit where the water was evaporated from the adhesive without raising the product temperature (i.e., web temperature) above 215 degrees Fahrenheit. Upon exiting the oven, polyethylene foam that that had been recently corona discharge treated (to raise surface energy to at least 40 dynes) was laminated to the adhesive. The patches were then cut into pre-selected shape and size, preferably ⅝" diameter circles.

It should be noted that the above description, attached figure and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A shelf stable composition useful for the transdermal delivery of vitamin $B_{12}$ to a subject, consisting of:
    (a) vitamin $B_{12}$ at 0.1 wt % to 15.0 wt %;
    (b) sodium selenite at 0.01 wt % to 1.0 wt %;
    (c) menthone at 0.8 wt % to 12.0 wt %;
    (d) propylene glycol at 0.5 wt % to 12.0 wt %;
    (e) nonionic surfactant at 0.1% to 1.0 wt %
    (f) polyurethane polymer associative thickener at 0.6 wt % to 6.0 wt %;
    (g) added water at 0.3 wt % to 50 wt %; and
    (h) acrylic co-polymer at 40.0 wt % to 97.6 wt %.

2. A shelf stable transdermal delivery patch comprising the composition set forth in claim 1 after evaporation of the 0.3 wt % to 50 wt % added water content.

3. A method of manufacturing a shelf stable transdermal delivery patch for transdermally delivering vitamin $B_{12}$ to a subject, said method comprising:
    (a) roller-coating a composition consisting of:
        (i) vitamin $B_{12}$ at 0.1 wt % to 15.0 wt %;
        (ii) sodium selenite at 0.01 wt % to 1.0 wt %;
        (iii) menthone at 0.8 wt % to 12.0 wt %;
        (iv) propylene glycol at 0.5 wt % to 12.0 wt %;
        (v) nonionic surfactant at 0.1% to 1.0 wt %
        (vi) polyurethane polymer associative thickener at 0.6 wt % to 6.0 wt %;
        (vii) added water at 0.3 wt % to 50 wt %; and
        (viii) acrylic co-polymer at 40.0 wt % to 97.6 wt %;
    onto an impermeable release layer to form a skin contact adhesive layer adjacent to said release layer;
    (b) evaporating the water from said composition by heating the composition to a temperature no greater than 215 degrees F.;
    (c) laminating a backing layer to said skin contact adhesive layer; and
    (d) cutting a multilayered product formed in steps (a)-(c) into a pre-selected shape and size thereby providing a shelf stable transdermal delivery patch.

4. A shelf stable transdermal delivery patch provided by the method set forth in claim 3.

* * * * *